(12) United States Patent
Robbins

(10) Patent No.: US 12,064,355 B1
(45) Date of Patent: *Aug. 20, 2024

(54) SPINAL INTERBODY IMPLANTS

(71) Applicant: Alevio, LLC, Birmingham, AL (US)

(72) Inventor: Joseph T. Robbins, Vestavia Hills, AL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/504,410

(22) Filed: Oct. 18, 2021

Related U.S. Application Data

(63) Continuation of application No. 16/877,437, filed on May 18, 2020, now Pat. No. 11,173,043.

(60) Provisional application No. 62/849,346, filed on May 17, 2019.

(51) Int. Cl.
*A61F 2/44* (2006.01)
*A61F 2/28* (2006.01)
*A61F 2/30* (2006.01)

(52) U.S. Cl.
CPC ...... *A61F 2/447* (2013.01); *A61F 2002/2835* (2013.01); *A61F 2002/30131* (2013.01); *A61F 2002/30952* (2013.01); *A61F 2002/30985* (2013.01); *A61F 2310/00023* (2013.01); *A61F 2310/00029* (2013.01); *A61F 2310/00071* (2013.01)

(58) Field of Classification Search
CPC .. A61F 2/44; A61F 2/442; A61F 2/445; A61F 2/446; A61F 2/4465; A61F 2/447
See application file for complete search history.

(56) References Cited

U.S. PATENT DOCUMENTS 6,461,359 B1 * 10/2002 Tribus ............... A61B 17/7059
  606/279
7,018,416 B2 * 3/2006 Hanson ............. A61B 17/1671
  623/17.16
7,232,463 B2 * 6/2007 Falahee ................ A61B 90/92
  623/17.11

(Continued)

FOREIGN PATENT DOCUMENTS

FR 2923155 A1 5/2009
WO 2009/091775 A2 7/2009

(Continued)

OTHER PUBLICATIONS

T Serra et al., "Design and fabrication of 3D-printed anatomically shaped lumbar cage for intervertebral disc (IVD) degeneration treatment", Biofabrication, vol. 8, Jul. 2016, 11 Pages.

*Primary Examiner* — Eric S Gibson
(74) *Attorney, Agent, or Firm* — C. Brandon Browning; Maynard Nexsen PC

(57) ABSTRACT

Spinal interbody fusion implants for use in posterior lumbar interbody fusions (PLIF), anterior lumbar interbody fusions (ALIF), transforaminal lumbar interbody fusions (TLIF) and transpsoas interbody fusions (DLIF), each of the implants including a 3-D printed titanium frame having meshed sidewalls, open top and bottom faces and a selectively closeable back plate for enclosing a posterior end of the frame. A machined, acid treated allograft bone graft is contained within the frame, the bone graft having a window for containing a biomaterial, anti-migration teeth and a ridge configured to mate with a slot within the frame for locking the graft in the frame.

15 Claims, 20 Drawing Sheets

(56) References Cited

U.S. PATENT DOCUMENTS

| | | | |
|---|---|---|---|
| 7,503,933 B2 | 3/2009 | Michelson | |
| 7,641,690 B2 | 1/2010 | Abdou | |
| 7,658,766 B2 | 2/2010 | Melkent et al. | |
| 8,088,163 B1* | 1/2012 | Kleiner | A61F 2/442 |
| | | | 623/17.11 |
| 8,491,658 B1* | 7/2013 | Etminan | A61F 2/4611 |
| | | | 623/17.16 |
| 8,617,245 B2 | 12/2013 | Brett | |
| 8,628,576 B2 | 1/2014 | Triplett et al. | |
| 8,858,637 B2 | 10/2014 | Milz et al. | |
| 9,060,876 B1* | 6/2015 | To | A61F 2/442 |
| 9,402,736 B2* | 8/2016 | Etminan | A61F 2/30744 |
| 9,883,953 B1* | 2/2018 | To | A61F 2/442 |
| 9,913,732 B2* | 3/2018 | Kana | A61F 2/30744 |
| 9,968,461 B2* | 5/2018 | Zappacosta | A61F 2/4455 |
| 9,987,051 B2 | 6/2018 | Nunley et al. | |
| 10,092,403 B2* | 10/2018 | Costabile | A61B 5/150992 |
| 10,117,746 B2 | 11/2018 | Cordaro | |
| 10,179,053 B2* | 1/2019 | Zappacosta | A61F 2/447 |
| 10,610,375 B2* | 4/2020 | Quinlan | A61F 2/447 |
| 10,925,750 B2* | 2/2021 | Zappacosta | A61F 2/447 |
| 11,173,043 B1* | 11/2021 | Robbins | A61F 2/4455 |
| 2005/0071008 A1* | 3/2005 | Kirschman | A61B 17/8047 |
| | | | 606/328 |
| 2008/0269806 A1* | 10/2008 | Zhang | A61F 2/4455 |
| | | | 606/280 |
| 2009/0030519 A1* | 1/2009 | Falahee | A61F 2/447 |
| | | | 623/17.11 |
| 2009/0105830 A1* | 4/2009 | Jones | A61F 2/4465 |
| | | | 606/301 |
| 2013/0297029 A1* | 11/2013 | Kana | A61F 2/4455 |
| | | | 623/17.16 |
| 2014/0107786 A1* | 4/2014 | Geisler | A61F 2/447 |
| | | | 623/17.16 |
| 2015/0328009 A1* | 11/2015 | Zappacosta | A61F 2/4455 |
| | | | 623/17.16 |
| 2015/0328010 A1* | 11/2015 | Martynova | A61F 2/447 |
| | | | 623/17.16 |
| 2016/0022431 A1* | 1/2016 | Wickham | A61F 2/447 |
| | | | 623/17.16 |
| 2016/0199193 A1 | 7/2016 | Willis et al. | |
| 2017/0049579 A1* | 2/2017 | Quinlan | A61B 17/1604 |
| 2017/0258606 A1 | 9/2017 | Afzal | |
| 2018/0235772 A1* | 8/2018 | Zappacosta | A61F 2/4455 |
| 2018/0256336 A1 | 9/2018 | Mueller et al. | |
| 2019/0105175 A1* | 4/2019 | Zappacosta | A61F 2/4455 |
| 2019/0343644 A1* | 11/2019 | Ryan | A61F 2/30771 |
| 2019/0343645 A1* | 11/2019 | Miccio | A61F 2/4455 |
| 2020/0229939 A1* | 7/2020 | To | A61F 2/447 |

FOREIGN PATENT DOCUMENTS

| | | |
|---|---|---|
| WO | 2016/130878 A1 | 8/2016 |
| WO | 2017/106780 A1 | 6/2017 |
| WO | 2018/127574 A1 | 7/2018 |

\* cited by examiner

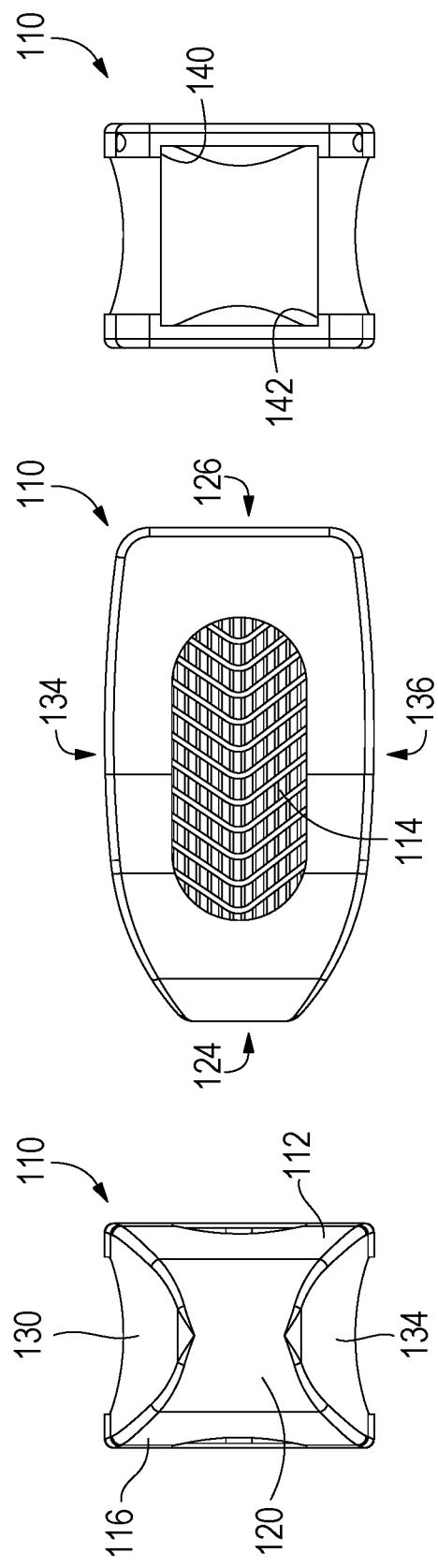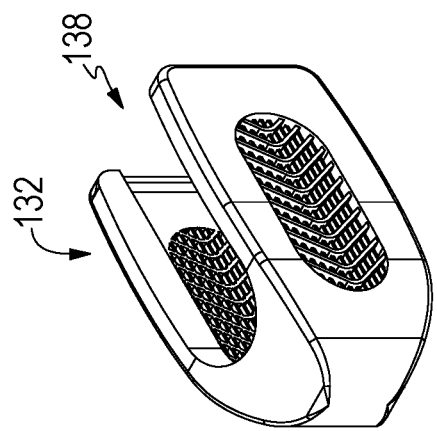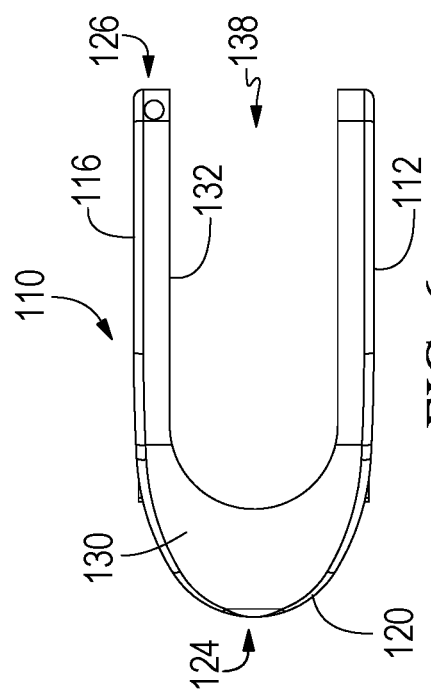

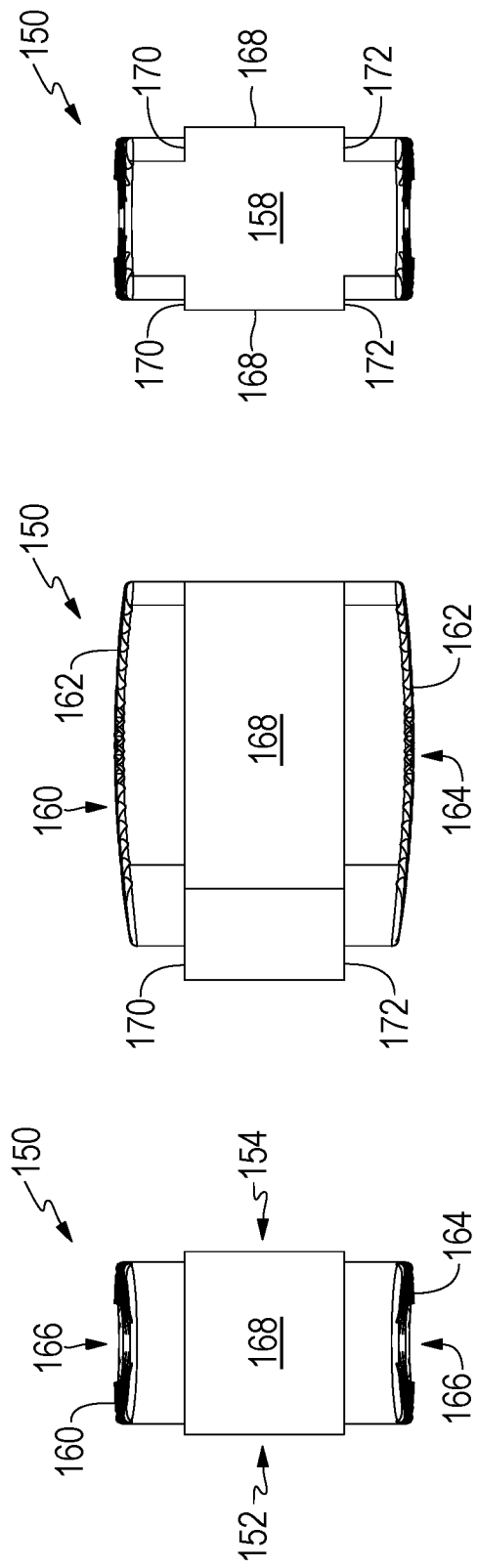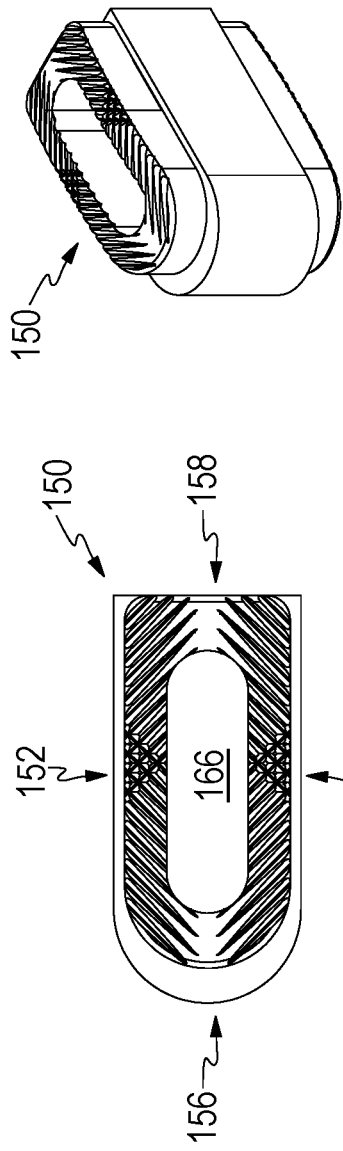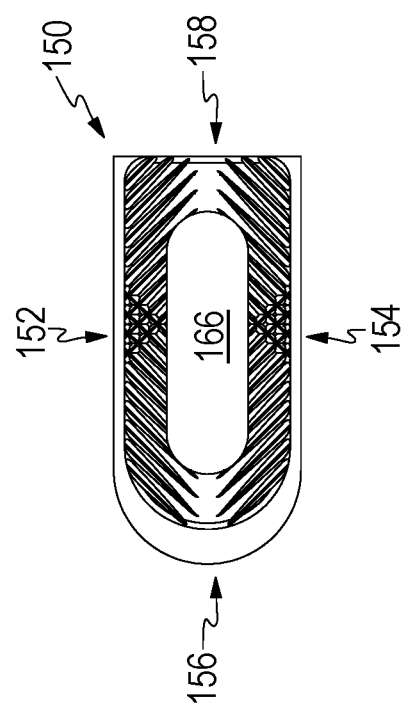

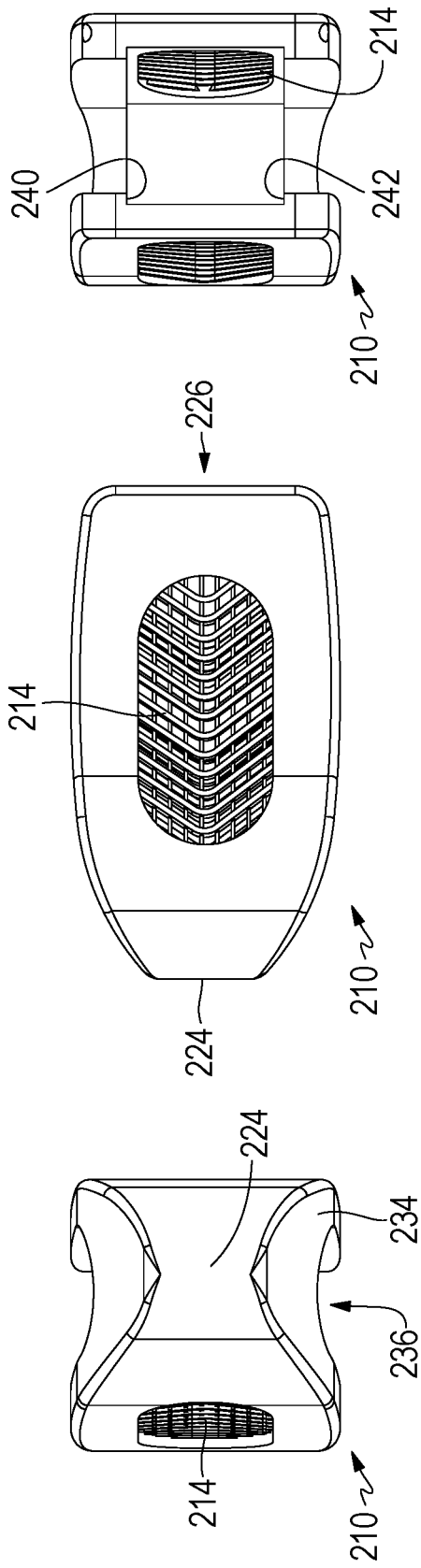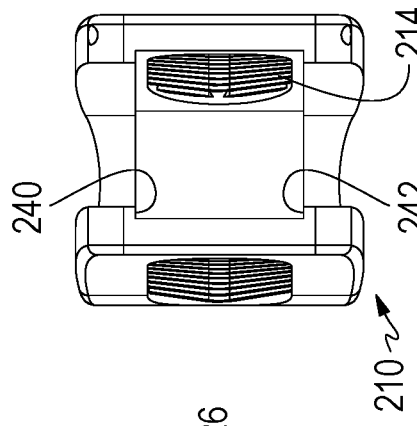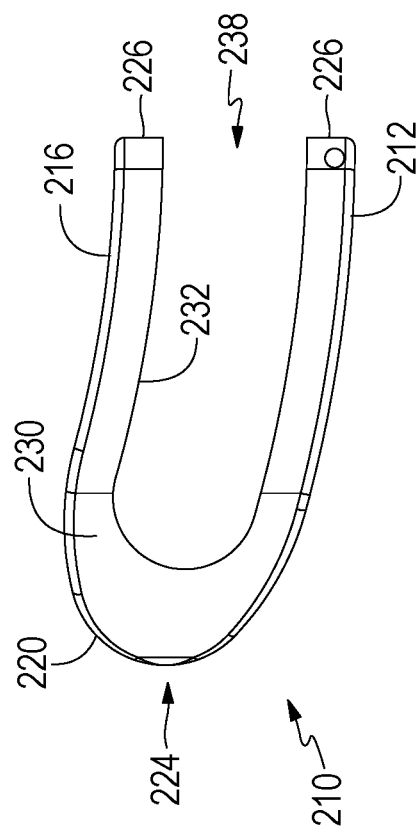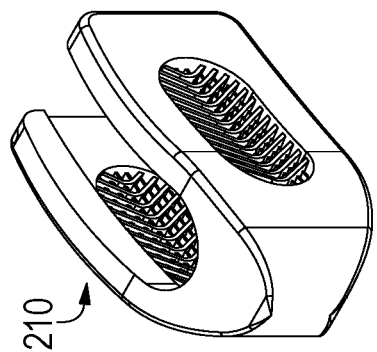

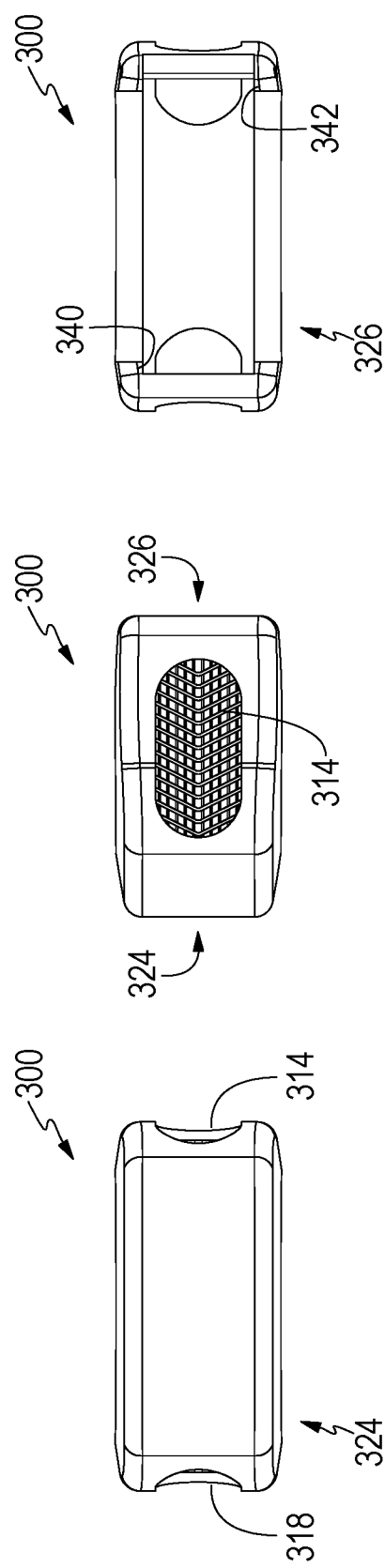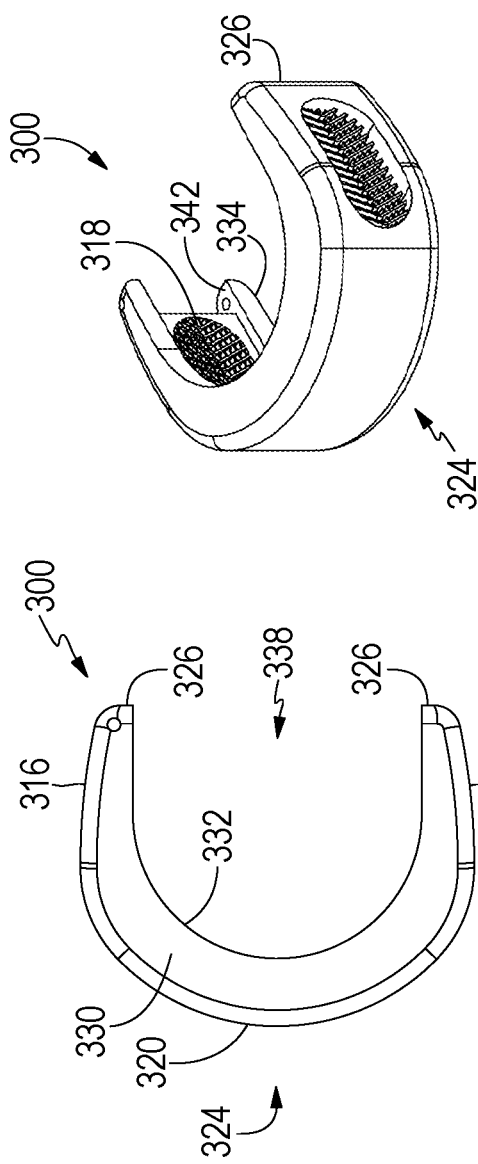

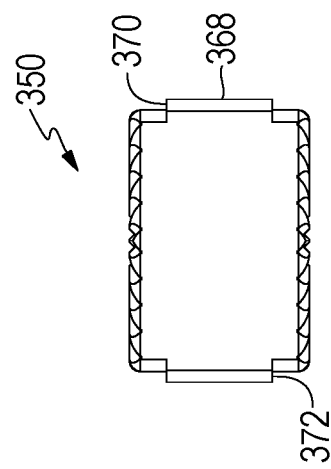
FIG. 44
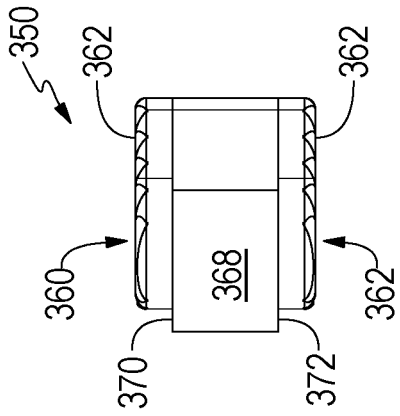
FIG. 43
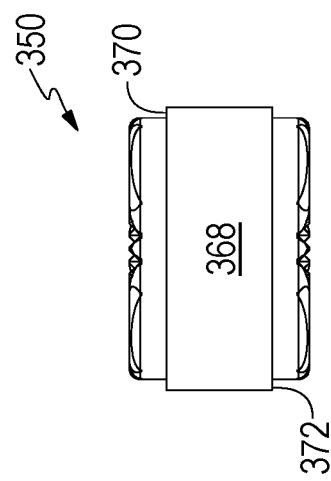
FIG. 42
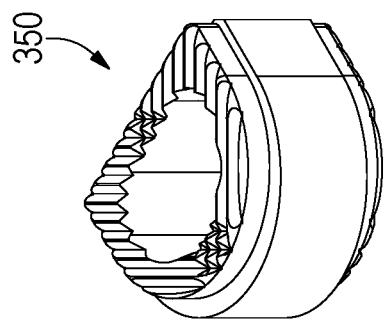
FIG. 46
FIG. 45

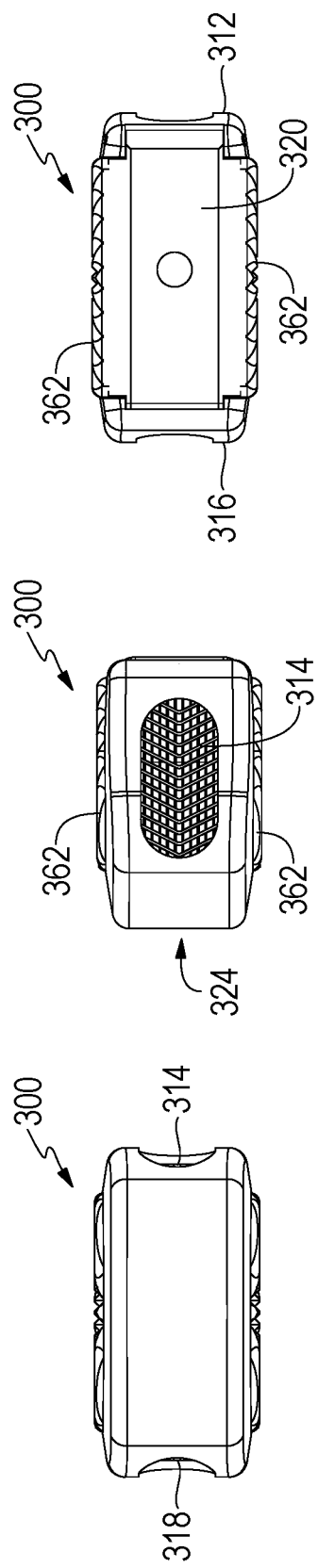
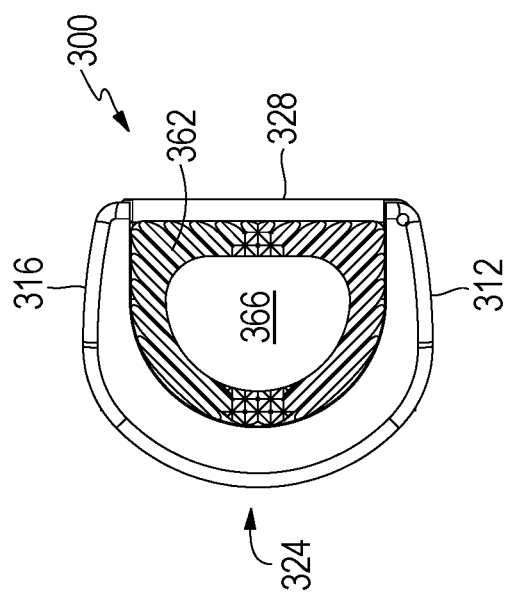
FIG. 50
FIG. 49
FIG. 51
FIG. 48

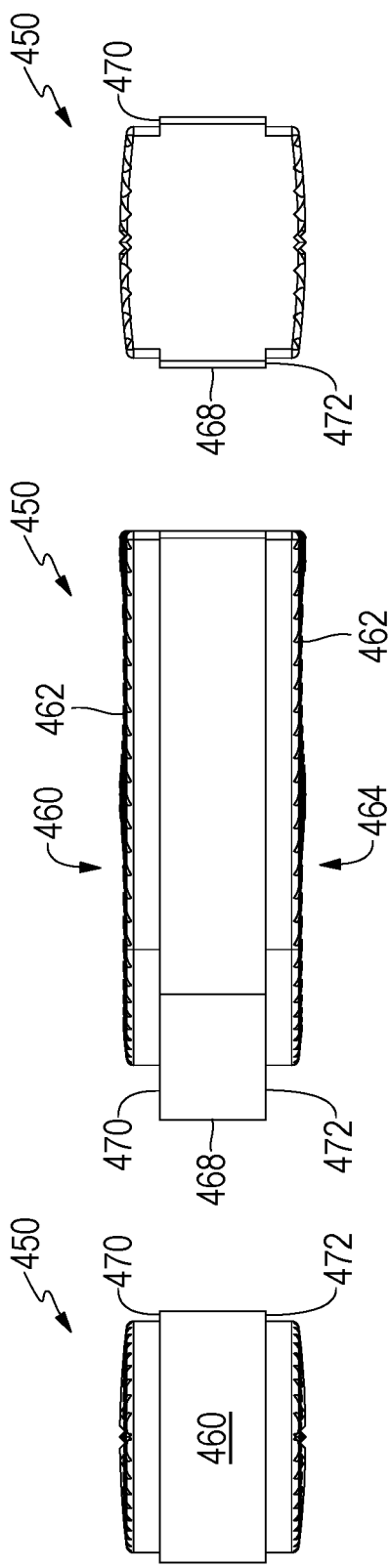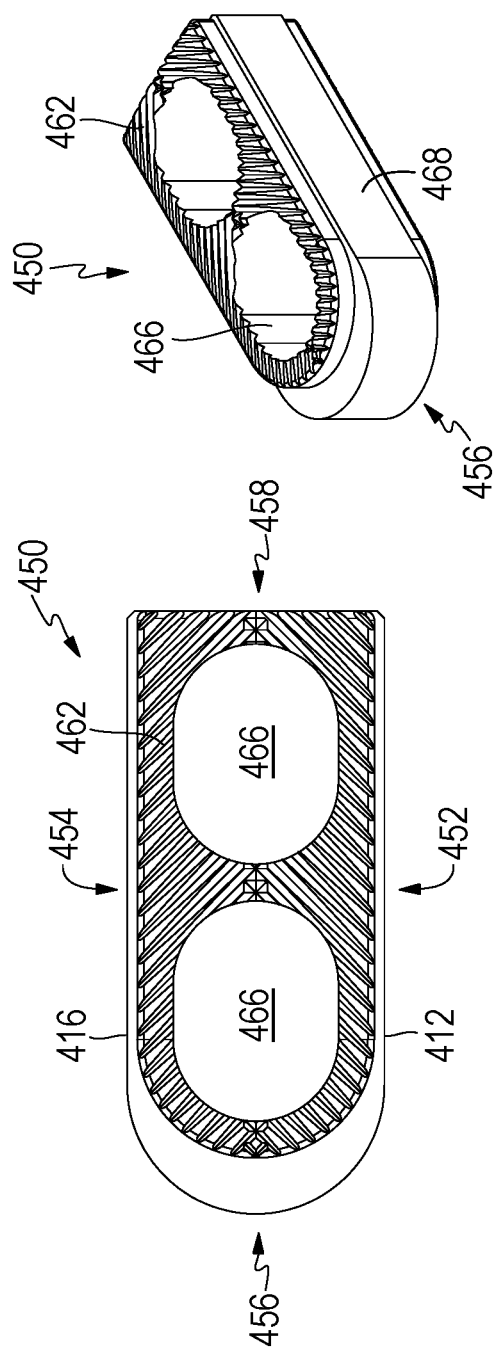

SPINAL INTERBODY IMPLANTS

RELATED APPLICATIONS

This application is a continuation of and claims priority to U.S. Non-provisional patent application Ser. No. 16/877,437, titled, "Spinal Interbody Implants, filed on May 18, 2020, which claims priority to U.S. Provisional Patent Application No. 62/849,346, titled, "Spinal Interbody Implants," filed on May 17, 2019, the entire contents of which are incorporated herein by reference.

FIELD OF USE

The present invention is directed to spinal implants and, more particularly, to spinal interbody fusion implants for use in posterior lumbar interbody fusions (PLIF), anterior lumbar interbody fusions (ALIF), transforaminal lumbar interbody fusions (TLIF) and transpsoas interbody fusions (DLIF), each of the implants including a 3-D printed titanium frame having meshed sidewalls, open top and bottom faces and a selectively closeable back-plate for enclosing a posterior end of the frame and a machined, acid treated allograft bone graft contained within the frame, the bone graft having anti-migration teeth and a window for containing a biomaterial.

BACKGROUND OF INVENTION

Spinal fusion, also called spondylodesis or spondylosyndesis, is a neurosurgical or orthopedic surgical technique that joins two or more vertebrae. The procedure can be performed at any level in the spine (cervical, thoracic, or lumbar) and prevents any movement between the fused vertebrae. There are many types of spinal fusion and each technique involves using bone grafting, either from the patient (autograft), donor (allograft), or artificial bone substitutes, to help the bones heal together.

Interbody fusion is a graft where the entire intervertebral disc between vertebrae is removed, and a bone graft is placed in the space between the vertebra. A plastic or titanium device may be placed between the vertebra to maintain spine alignment and disc height. The types of interbody fusion are (1) anterior lumbar interbody fusion (ALIF), where the disc is accessed from an anterior abdominal incision, (2) aosterior lumbar interbody fusion (PLIF), where the disc is accessed from a posterior incision, (3) transforaminal lumbar interbody fusion (TLIF) where the disc is accessed from a posterior incision on one side of the spine, (4) transpsoas interbody fusion (DLIF), where the disc is accessed from an incision through the psoas muscle on one side of the spine, and (5) oblique lateral lumbar interbody fusion (OLLIF), where the disc is accessed from an incision through the psoas muscle obliquely.

Exemplary spinal interbody implants are disclosed in U.S. Patent Application Publication No. 2018/0256336; France Patent Document No. FR2923155A; and U.S. Pat. No. 7,641,690.

PLIF

A PLIF is a surgery designed to stop the motion at the targeted segment of the spine. A PLIF is done in the lumbar, or lower, spine. Most commonly it is performed on the L4-L5 or L5-S1 segment at the bottom of the lumbar spine. This surgery may be done to treat lumbar degenerative disc disease, in which a degenerated disc becomes painful. It may also be done for a lumbar spondylolisthesis, in which one vertebra slips forward over the vertebra below it. A PLIF starts with a three to six-inch long incision in the midline of the back. Next, the lower back muscles, called erector spinae, are stripped off the lamina on both sides and at multiple levels. The lamina is removed, which allows visualization of the nerve roots. The facet joints, which are directly over the nerve root, may then be trimmed to give the nerve roots more room. The nerve roots are then retracted to one side and the disc space is cleaned of the disc material. Some type of implant, called a cage, is then inserted into the disc space. The cage helps restore more of the normal spacing in between the vertebrae, alleviating pressure on the nerve roots. Bone graft is placed in the cage and along the sides of the spine. There are many bone graft options. If the patient's own bone graft is used, bone morsels are harvested from the patient's iliac crest, along the back of the hip. This is an additional surgical procedure that is done at the same time as the fusion surgery. Bone that has been removed from a laminectomy may also be used, or synthetic bone graft options may be used. The surgeon may implant a series of screws and rods to the back of the spine for additional support. A PLIF fusion may be supplemented by a simultaneous posterolateral spine fusion surgery. In addition to open surgery, a PLIF may sometimes be done through a tube in a minimally invasive approach.

TLIF

TLIF back surgery is done through the posterior (back) part of the spine. Surgical hardware is applied to the spine to help enhance the fusion rate. Pedicle screws and rods are attached to the back of the vertebra and an interbody fusion spacer is inserted into the disc space from one side of the spine. Bone graft is placed into the interbody space and alongside the back of the vertebra to be fused. Bone graft is obtained from the patient's pelvis, although bone graft substitutes are also sometimes used. As the bone graft heals, it fuses the vertebra above and below and forms one long bone. TLIF fuses the anterior (front) and posterior (back) columns of the spine through a single posterior approach. The anterior portion of the spine is stabilized by the bone graft and interbody spacer. The posterior column is locked in place with pedicle screws, rods, and bone graft. TLIF procedure has several theoretical advantages over some other forms of lumbar fusion: Bone fusion is enhanced because bone graft is placed both along the gutters of the spine posteriorly but also in the disc space. A spacer is inserted into the disc space helping to restore normal height and opening up nerve foramina to take pressure off the nerve roots. A TLIF procedure allows the surgeon to insert bone graft and spacer into the disc space from a unilateral approach laterally without having to forcefully retract the nerve roots as much, which may reduce injury and scarring around the nerve roots when compared to a PLIF procedure. Pedicle screws are placed into the vertebra. Exposure of the disc space is done on one side by removing the facet joints and protecting the nerve roots. The disc space is entered and disc material is removed. Bone graft is obtained from the patient's iliac crest (the hip). A spacer or interbody cage that is filled with bone graft is placed into the disc space to maintain the disc height. Additional bone is placed in the lateral (side) gutters of the vertebra and the disc space. Pedicle screws are attached to rods or plates. The wound is closed.

ALIF

An ALIF is designed to stop the motion at the symptomatic segment of the spine. An ALIF is done in the lumbar, or lower, spine. Most commonly it is performed on the L4 through L5 or L5 through Si segment at the bottom of the lumbar spine, as these segments are most likely to break down. An ALIF is most commonly done to treat lumbar degenerative disc disease, in which a degenerated disc becomes painful. It may be done for other indications and may be combined with a posterior approach as well, if added stability is needed. This type of fusion is unique as the surgery is done from the front, or anterior. It starts with a 3 to 5-inch long incision on the left side of the abdomen. Next, the abdomen muscles are retracted to the side. The abdominal contents lay inside a large sack (the peritoneum) that is then retracted to the side, allowing access to the front of the spine without actually entering the abdomen. The large blood vessels, called the aorta and vena cava, lay on top of the spine, so a vascular surgeon will usually be part of the surgery to move the large blood vessels to the side. After the blood vessels have been moved aside, the disc material is removed. Some type of implant, called a cage, is then inserted into the disc space. The cage helps restore more of the normal spacing in between the vertebrae, alleviating pressure on the nerve roots. Bone graft is placed in the cage and sometimes in front of the cage. Sometimes additional fixation is used by inserting screws through the cage. If the patient's own bone graft is used, bone morsels are harvested from the front of the patient's iliac crest, or hip bone. This is an additional surgical procedure that is done at the same time as the fusion surgery. Synthetic bone graft options are may also be used. In the months following the surgery, the bone graft heals together through and alongside the cage, creating one long bone between the vertebrae and immobilizing that segment of the spine. An ALIF may be combined with a simultaneous posterolateral fusion, with an approach from the back of the spine, if additional stability is needed to help ensure a successful fusion.

DLIF

DLIF procedure involves a small skin incision in a patient's side (therefore, direct lateral). Using minimally invasive surgical techniques, the neurosurgeon separates muscles (psoas muscle) and soft tissues to access the intervertebral disc. Because access to the spine is through the psoas muscle, DLIF is sometimes called a trans-psoas LIF or approach. The patient is given general anesthesia. The surgeon then makes two small incisions in the side of the patient. These incisions are very small as compared to the traditional incisions made in the back surgery procedures. The surgeon inserts a probe in one of the incisions. The probe stimulates and detects the nerves around the spine and helps the surgeon to avoid the nerves and to leave them undamaged. The surgeon uses the second incision to help guide the surgical instruments. When the probe reaches at the proper position, the surgeon inserts a series of dilation tubes over the probe. This helps to create a larger opening. The surgeon then inserts a retraction device over the dilation tubes. This device helps to move aside the muscle tissues and to provide access to the spine. The surgeon operates through the channel created by the retractor device and removes the damaged disc. The surgeon then places an implant filled with bone graft in the empty disc space. The implant realigns the vertebral bones and lifts pressure from the pinched spinal nerves. The bone graft will grow and form a fusion to connect the vertebral bodies. The retractor device is removed and the incisions are closed. The wounds are cleaned and medical bandage is applied

SUMMARY OF INVENTION

The present invention is directed to spinal interbody fusion implants for use in posterior lumbar interbody fusions (PLIF), anterior lumbar interbody fusions (ALIF), transfo-raminal lumbar interbody fusions (TLIF) and transpsoas interbody fusions (DLIF). According to one aspect of the invention, there is provided a spinal implant including a 3-D printed titanium enclosure and a CNC machined, acid treated allograft bone graft contained within the enclosure.

The enclosure includes a first sidewall, a first mesh window extending through the first sidewall, a second sidewall opposing the first sidewall, a second mesh window extending through the second sidewall, a substantially convex third sidewall extending to and between the first sidewall and the second sidewall, the third sidewall forming a first end of the enclosure, a second end opposite the first end, a fourth sidewall opposing the third sidewall and hingedly coupled to the first sidewall and detachably coupled to the second sidewall, the a longitudinal axis extending through a center of the third sidewall and a center of the fourth sidewall, a substantially U-shaped top wall with a substantially U-shaped top opening there through, and a substantially U-shaped bottom wall with a substantially U-shaped bottom opening there through. The first sidewall, the second sidewall and the third sidewall form a substantially U-shaped sidewall defining a substantially U-shaped slot having an upper seat portion and a lower seat portion.

The allograft bone graft includes a first face, a second face opposing the first face, a substantially convex third face extending to and between the first face and the second face, wherein the longitudinal axis extends through a center of the third face, a fourth face opposing the third face having a substantially cross-shaped cross-section, wherein the longitudinal axis extends through a center of the fourth face, a top face including anti-migration ridges, a bottom face including anti-migration ridges, and a hole extending to and between the top face and the bottom face. The first face, the second face and the third face form a substantially U-shaped face including a substantially U-shaped protrusion extending along a length of the U-shaped face and defining a graft upper ledge and a graft lower ledge. The bone graft is provided as a unitary block of bone. The block of bone may be treated or machined to include openings therein and there through or to increase porosity of the block.

In one embodiment, the allograft bone graft is contained within the enclosure with the a graft upper ledge engaged with the upper seat portion and the graft lower ledge engaged with the lower seat portion. In another embodiment, the top face and the bottom face taper inwardly toward the longitudinal axis at the first end of the enclosure. In another embodiment, the first sidewall and the second sidewall are parallel. In another embodiment, the top face and the bottom face are convex. In another embodiment, the top face extends out of the enclosure through the top opening and the bottom face extends out of the enclosure through the bottom opening. In another embodiment, the fourth sidewall is fabricated from nickel titanium alloy or cobalt. In another embodiment, the implant includes a biomaterial contained within the hole extending to and between the top face and the bottom face. In another embodiment, the first sidewall is convex and the second sidewall is concave. In another embodiment, the first face is convex and the second face is concave. In another embodiment, the allograft bone graft is pre-hydrated. In another embodiment, the first sidewall, the second sidewall, the third sidewall, the top wall and the bottom wall are porous. In another embodiment, the first sidewall and the second sidewall taper inwardly towards the longitudinal axis at the second end of the enclosure. In another embodiment, the first face and the second face taper inwardly towards the longitudinal axis at the second end of the enclosure. In another embodiment, the top face and the bottom face are parallel. In yet another embodiment, the implant includes a third mesh window extending through the first sidewall and a fourth mesh window extending through the second sidewall. In another embodiment, the implant includes a second hole extending to and between the top face and the bottom face.

According to a second aspect of the invention, there is provided a surgical method for vertebral interbody fusion including providing a spinal implant including a 3-D printed titanium enclosure and a CNC machined, acid treated allograft bone graft contained within the enclosure and inserting one or more of the spinal implants between a first vertebra and a second vertebra. The surgical method may be a surgical procedure a posterior lumbar interbody fusion (PLIF) procedure, an anterior lumbar interbody fusion (ALIF) procedure, a transforaminal lumbar interbody fusion (TLIF) procedure or a transpsoas interbody fusions (DLIF) procedure.

BRIEF DESCRIPTION OF THE DRAWINGS

FIG. 3 is a elevational view of an anterior end of the cage of the PLIF implant of FIG. 01.
FIG. 4 is a elevational view of a lateral side of the cage of FIG. 3.
FIG. 5 is a elevational view of a posterior end of cage of FIG. 3.
FIG. 6 is a top plan view of the cage of FIG. 3.
FIG. 7 is a perspective view of the cage of FIG. 3.
FIG. 8 is a elevational view of an anterior end of the graft of the PLIF implant of FIG. 1.
FIG. 9 is a elevational view of a lateral side of the graft of FIG. 8.
FIG. 10 is a elevational view of a posterior end of graft of FIG. 8.
FIG. 11 is a top plan view of the graft of FIG. 8.
FIG. 12 is a perspective view of the graft of FIG. 8.
FIG. 20 is a elevational view of an anterior end of the cage of the TLIF implant of FIG. 18.
FIG. 21 is a elevational view of a lateral side of the cage of FIG. 20.
FIG. 22 is a elevational view of a posterior end of cage of FIG. 20.
FIG. 23 is a top plan view of the cage of FIG. 20.
FIG. 24 is a perspective view of the cage of FIG. 20.
FIG. 37 is a elevational view of an anterior end of the cage of the ALIF implant of FIG. 35.
FIG. 38 is a elevational view of a lateral side of the cage of FIG. 37.
FIG. 39 is a elevational view of a posterior end of cage of FIG. 37.
FIG. 40 is a top plan view of the cage of FIG. 37.
FIG. 41 is a perspective view of the cage of FIG. 37.
FIG. 42 is a elevational view of an anterior end of the graft of the ALIF implant of FIG. 35.
FIG. 43 is a elevational view of a lateral side of the graft of FIG. 42.
FIG. 44 is a elevational view of a posterior end of graft of FIG. 42.
FIG. 45 is a top plan view of the graft of FIG. 42.
FIG. 46 is a perspective view of the graft of FIG. 42.
FIG. 48 is a elevational view of THE anterior end of the ALIF implant of FIG. 35.
FIG. 49 is a elevational view of a lateral side of the ALIF implant of FIG. 35.
FIG. 50 is a elevational view of a posterior end of ALIF implant of FIG. 35.
FIG. 51 is a top plan view of the ALIF implant of FIG. 35.
FIG. 59 is a elevational view of an anterior end of the graft of the DLIF implant of FIG. 52.
FIG. 60 is a elevational view of a lateral side of the graft of FIG. 59.
FIG. 61 is a elevational view of a posterior end of graft of FIG. 59.
FIG. 62 is a top plan view of the graft of FIG. 59.
FIG. 63 is a perspective view of the graft of FIG. 59.

DETAILED DESCRIPTION

Figure 2:
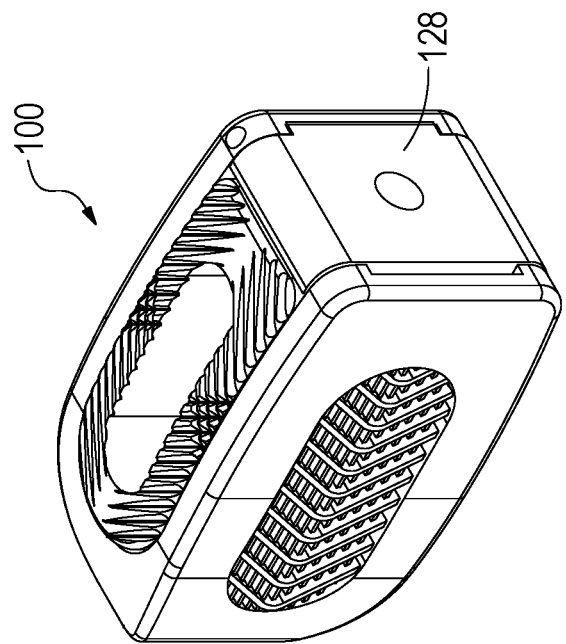
FIG. 2 is a perspective view of a posterior end of the PLIF implant of FIG. 01.
Figure 1:
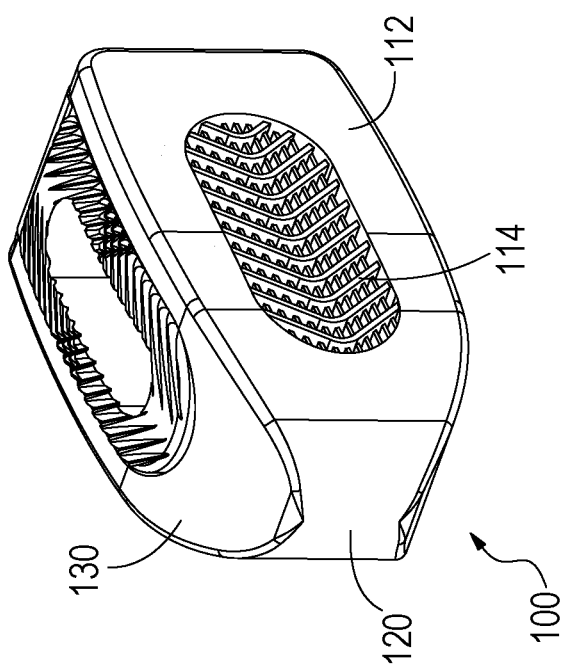
FIG. 1 is a perspective view of an anterior end of a PLIF implant illustrating an allograft bone graft contained with a cage.
Figure 13:
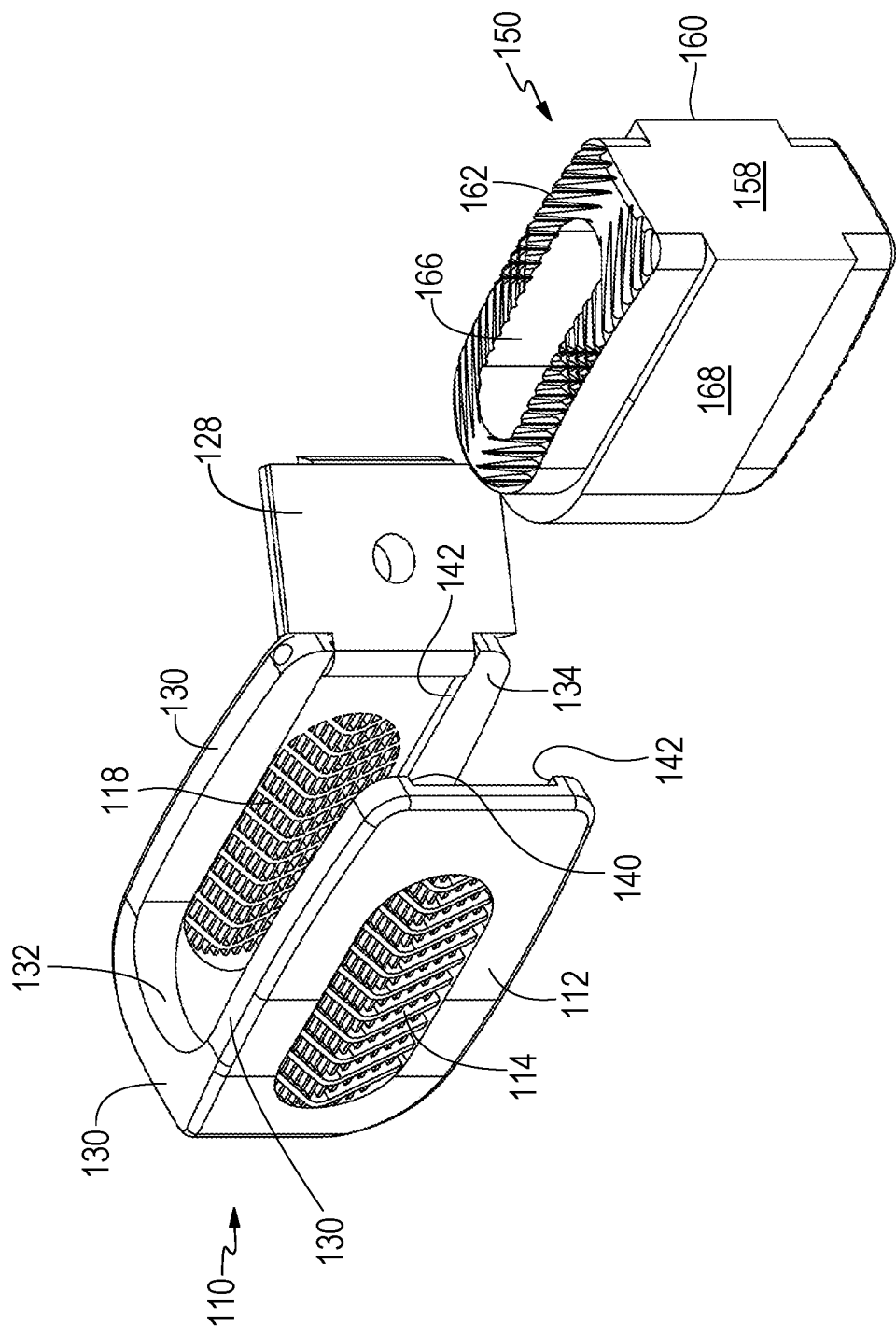
FIG. 13 is an exploded perspective view of the posterior end of the PLIF implant of FIG. 1.
Figure 16:
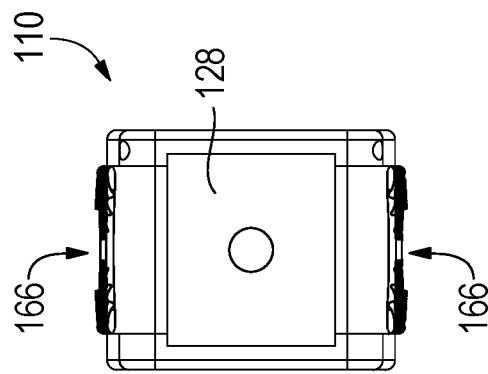
FIG. 16 is a elevational view of a posterior end of PLIF implant of FIG. 1.
Figure 15:
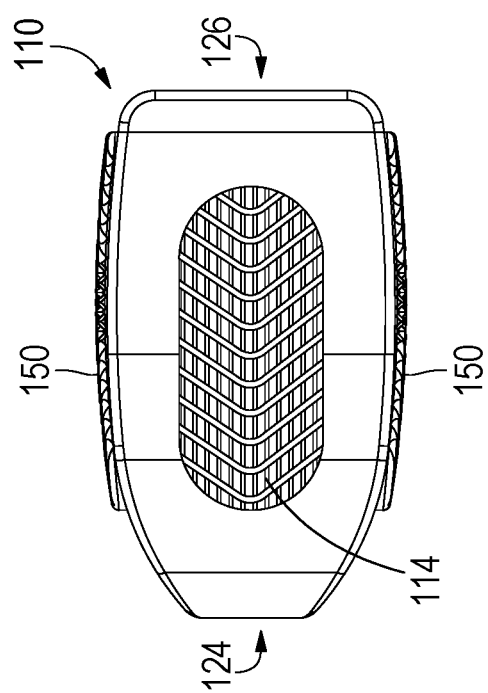
FIG. 15 is a elevational view of a lateral side of the PLIF implant of FIG. 1.
Figure 17:
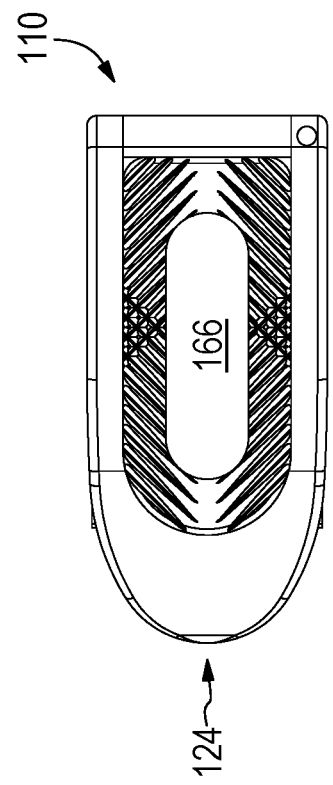
FIG. 17 is a top plan view of the PLIF implant of FIG. 1.
Figure 14:
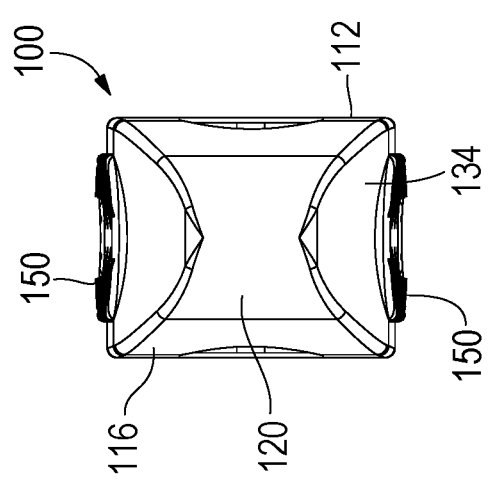
FIG. 14 is a elevational view of an anterior end of the PLIF implant of FIG. 1.
Figure 53:
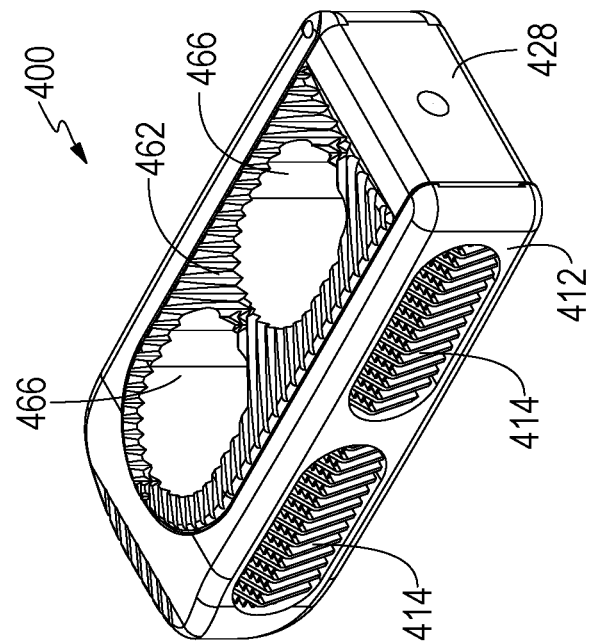
FIG. 53 is a perspective view of a posterior end of the DLIF implant of FIG. 52.
Figure 52:
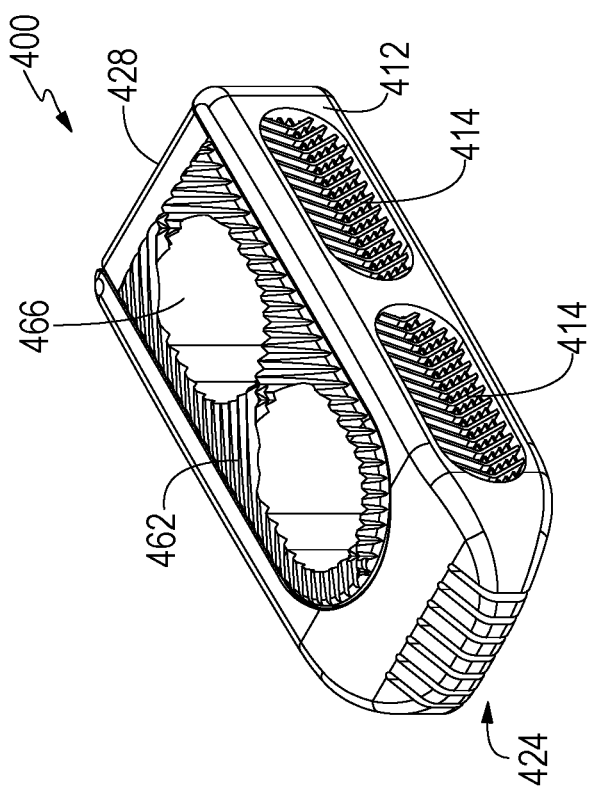
FIG. 52 is a perspective view of an anterior end of a DLIF implant illustrating an allograft bone graft contained with a cage.
Figure 56:
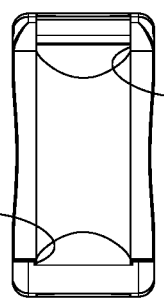
FIG. 56 is a elevational view of a posterior end of cage of FIG. 54.
Figure 58:
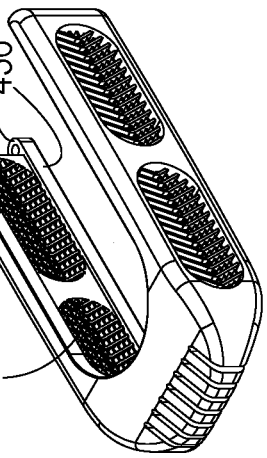
FIG. 58 is a perspective view of the cage of FIG. 54.
Figure 55:
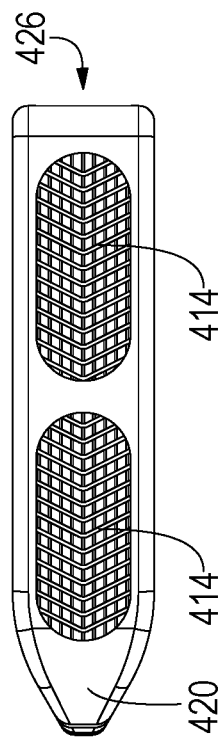
FIG. 55 is a elevational view of a lateral side of the cage of FIG. 54.
Figure 57:
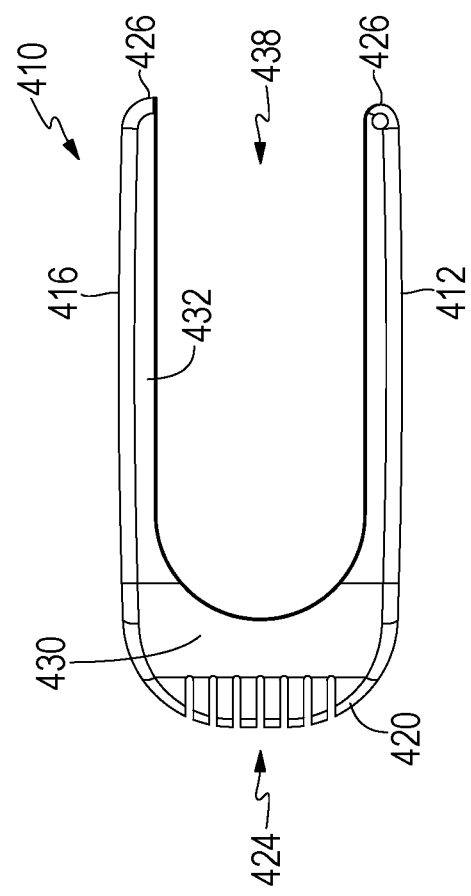
FIG. 57 is a top plan view of the cage of FIG. 54.
Figure 54:
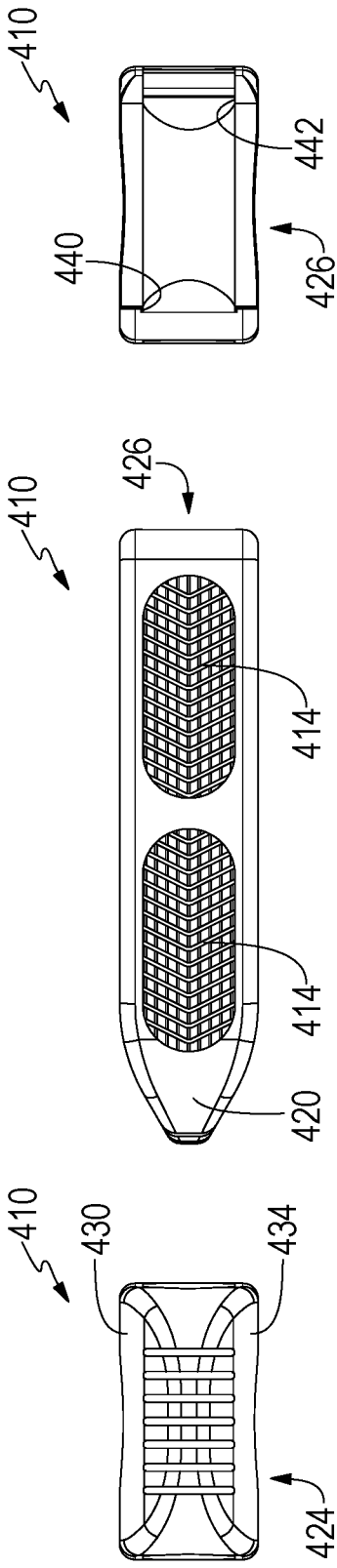
FIG. 54 is a elevational view of an anterior end of the cage of the DLIF implant of FIG. 52.
Figure 64:
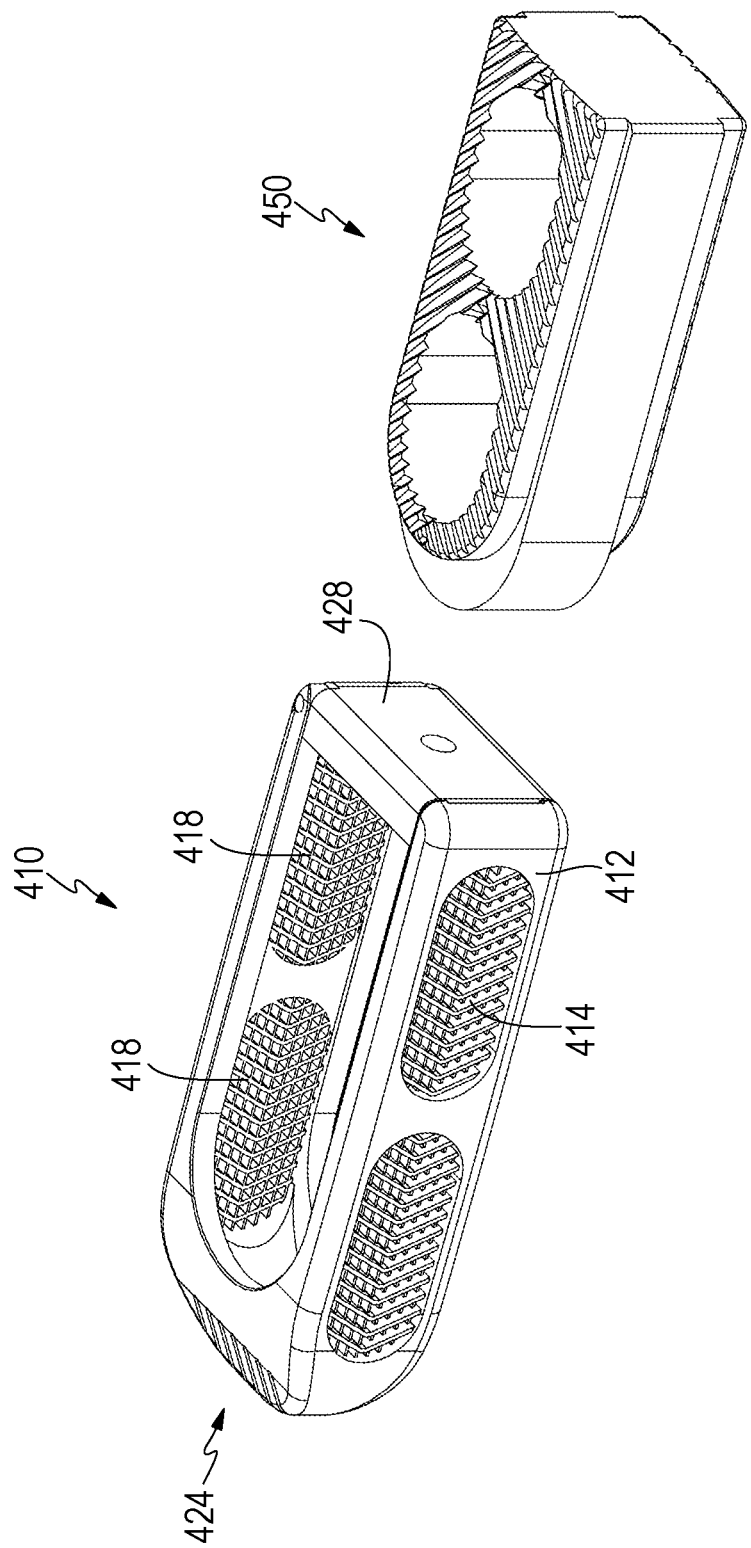
FIG. 64 is an exploded perspective view the posterior end of the DLIF implant of FIG. 52.
Figure 67:
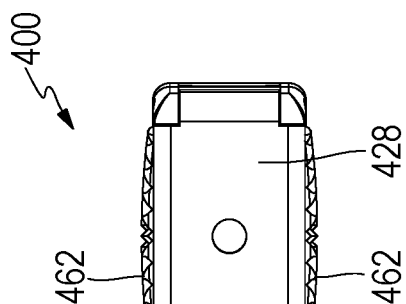
FIG. 67 is a elevational view of a posterior end of DLIF implant of FIG. 52.
Figure 66:
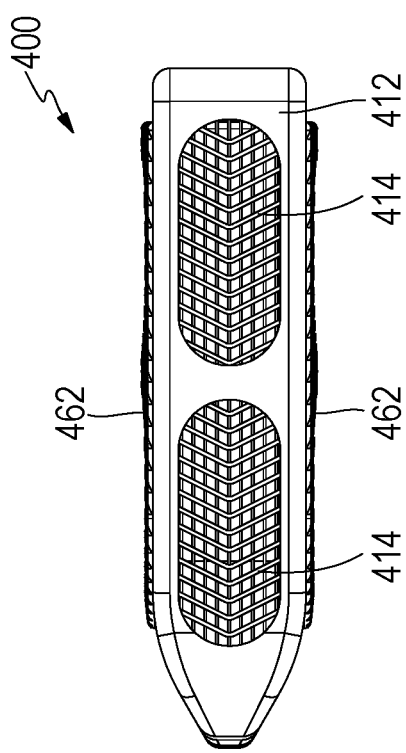
FIG. 66 is a elevational view of a lateral side of the DLIF implant of FIG. 52.
Figure 65:
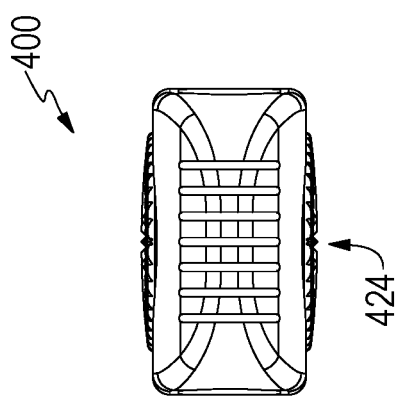
FIG. 65 is a elevational view of the anterior end of the DLIF implant of FIG. 52.
Figure 68:
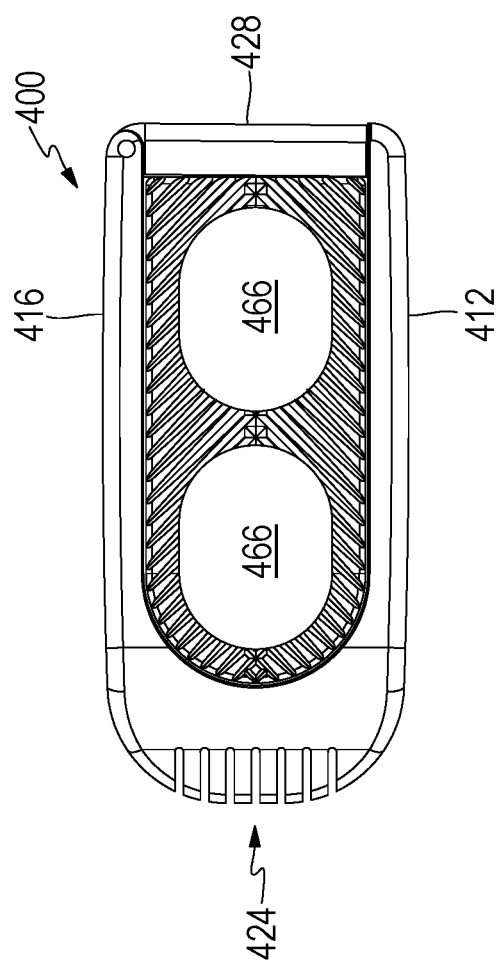
FIG. 68 is a top plan view of the DLIF implant of FIG. 52.

The present invention is directed to spinal interbody fusion implants for use in posterior lumbar interbody fusions (PLIF), anterior lumbar interbody fusions (ALIF), transforaminal lumbar interbody fusions (TLIF) and transpsoas interbody fusions (DLIF). FIGS. 1 through 17 depict a PLIF implant 100 in accordance with a first embodiment of the present invention. FIGS. 48 through 64 depict a TLIF implant 200 in accordance with a second embodiment of the present invention. FIGS. 65 through 81 depict an ALIF implant 300 in accordance with a third embodiment of the present invention, and FIGS. 82 through 98 depict a DLIF implant 400 in accordance with a fourth embodiment of the present invention. Generally, the spinal interbody fusion implants of the present invention include a 3-D printed titanium frame having meshed sidewalls, open top and bottom faces and a selectively closeable back plate for enclosing a posterior end of the frame. A machined, acid treated allograft bone graft is contained within the frame, the bone graft having a window for containing a biomaterial, anti-migration teeth and a ridge configured to mate with a slot within the frame for locking the graft in the frame.

PLIF

More particularly, referring to FIGS. 1 through 17, PLIF implant 100 includes a 3-D printed titanium enclosure 110 having a first sidewall 112, a first mesh window 114 extending through the first sidewall, a second sidewall 116 opposing the first sidewall, a second mesh window 118 extending through the second sidewall, a substantially convex third sidewall 120 extending to and between the first sidewall and the second sidewall, the third sidewall 120 forming a first end 124 of the enclosure, a second end 126 opposite the first end, a fourth sidewall 128 opposing the third sidewall and hingedly coupled to the second sidewall and detachably coupled to the first sidewall, a longitudinal axis extending through a center of the third sidewall and a center of the fourth sidewall, a substantially U-shaped top wall 130 with a substantially U-shaped top opening 132 there through, and a substantially U-shaped bottom wall 134 with a substantially U-shaped bottom opening 136 there through. The first sidewall, the second sidewall and the third sidewall form a substantially U-shaped sidewall defining a substantially U-shaped slot 138 having an upper seat portion 140 and a lower seat portion 142. As depicted in FIGS. 3 and 4, top wall 130 and bottom wall 134 taper inwardly toward first end 124.

PLIF allograft bone graft 150 includes a substantially convex first face 152, a substantially convex second face 154 opposing the first face, a substantially convex third face 156 extending to and between the first face and the second face, wherein the longitudinal axis extends through a center of the third face, a fourth face 158 opposing the third face having a substantially cross-shaped cross-section, wherein the longitudinal axis extends through a center of the fourth face, a top face 160 including anti-migration ridges 162, a bottom face 164 including anti-migration ridges 162, and a hole 166 extending to and between the top face and the bottom face. The first face, the second face and the third face form a substantially U-shaped face including a substantially U-shaped protrusion 168 extending along a length of the U-shaped face and defining a graft upper ledge 170 and a graft lower ledge 172.

In use, fourth sidewall 128 is pivoted open, and PLIF allograft bone graft 150 is inserted into enclosure 110 through the open doorway with the a graft upper ledge 170 engaged with the upper seat portion 140 and the graft lower ledge 172 engaged with the lower seat portion 142. Fourth sidewall 128 is then closed and fixed shut. Once assembled, PLIF implant 100 may be used to fuse adjacent vertebra according to the method described above, with top and bottom faces 160, 164 protruding out through U-shaped slot 138 so that anti-migration ridges 162 may directly contact adjacent the vertebrae.

TLIF

Figure 19:
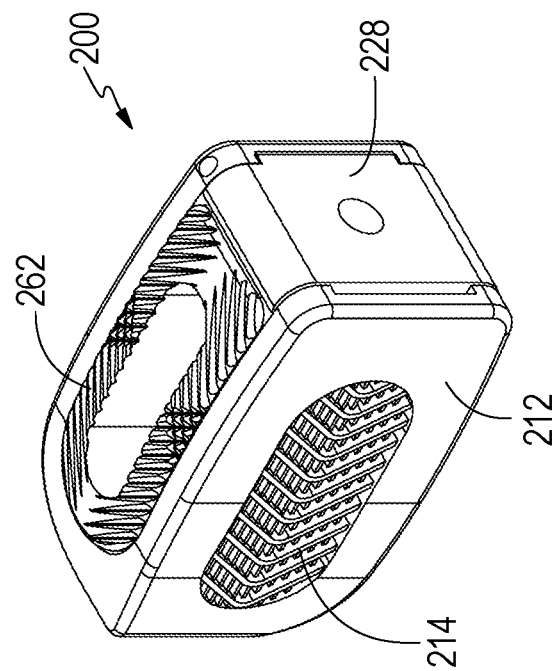
FIG. 19 is a perspective view of a posterior end of the TLIF implant of FIG. 18.
Figure 18:
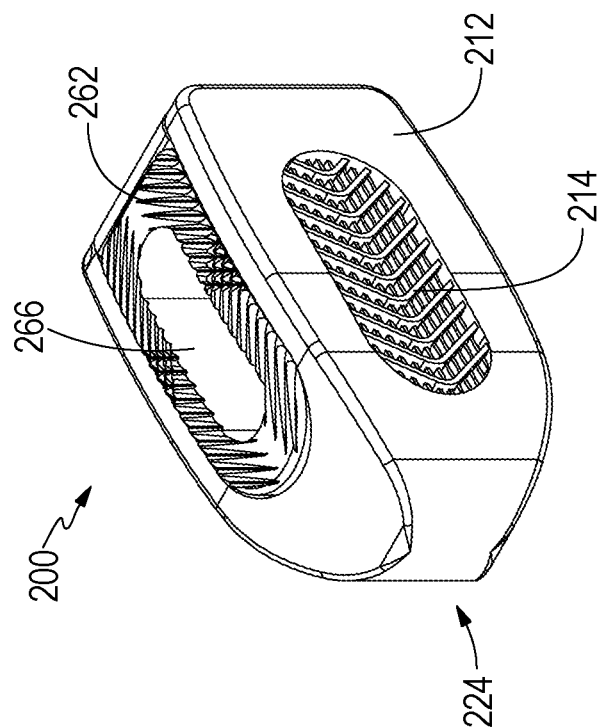
FIG. 18 is a perspective view of an anterior end of a TLIF implant illustrating an allograft bone graft contained with a cage.
Figure 25:
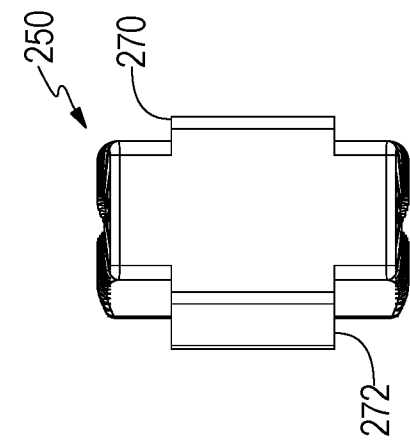
FIG. 25 is a elevational view of an anterior end of the graft of the TLIF implant of FIG. 18.
Figure 26:
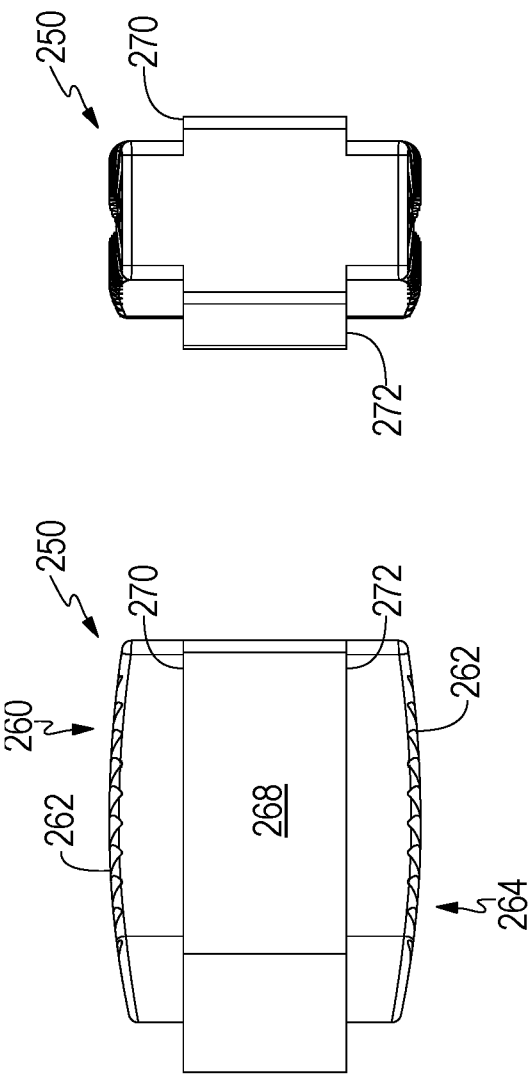
FIG. 26 is a elevational view of a lateral side of the graft of FIG. 25.
Figure 27:
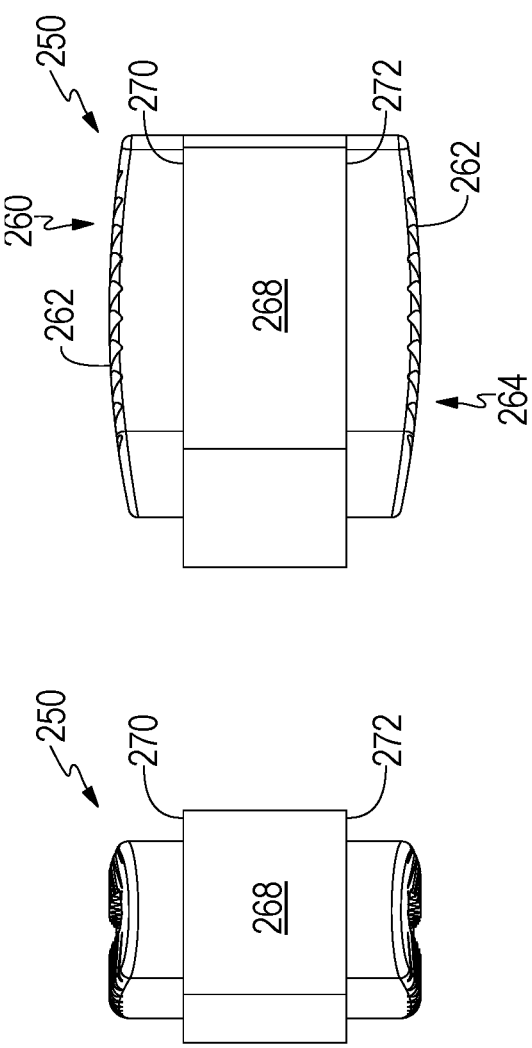
FIG. 27 is a elevational view of a posterior end of graft of FIG. 25.
Figure 28:
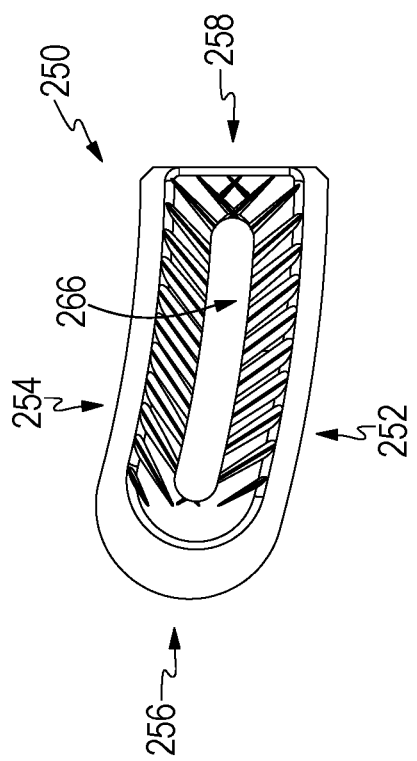
FIG. 28 is a top plan view of the graft of FIG. 25.
Figure 29:
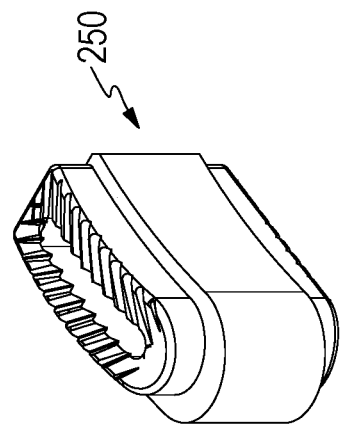
FIG. 29 is a perspective view of the graft of FIG. 25.
Figure 30:
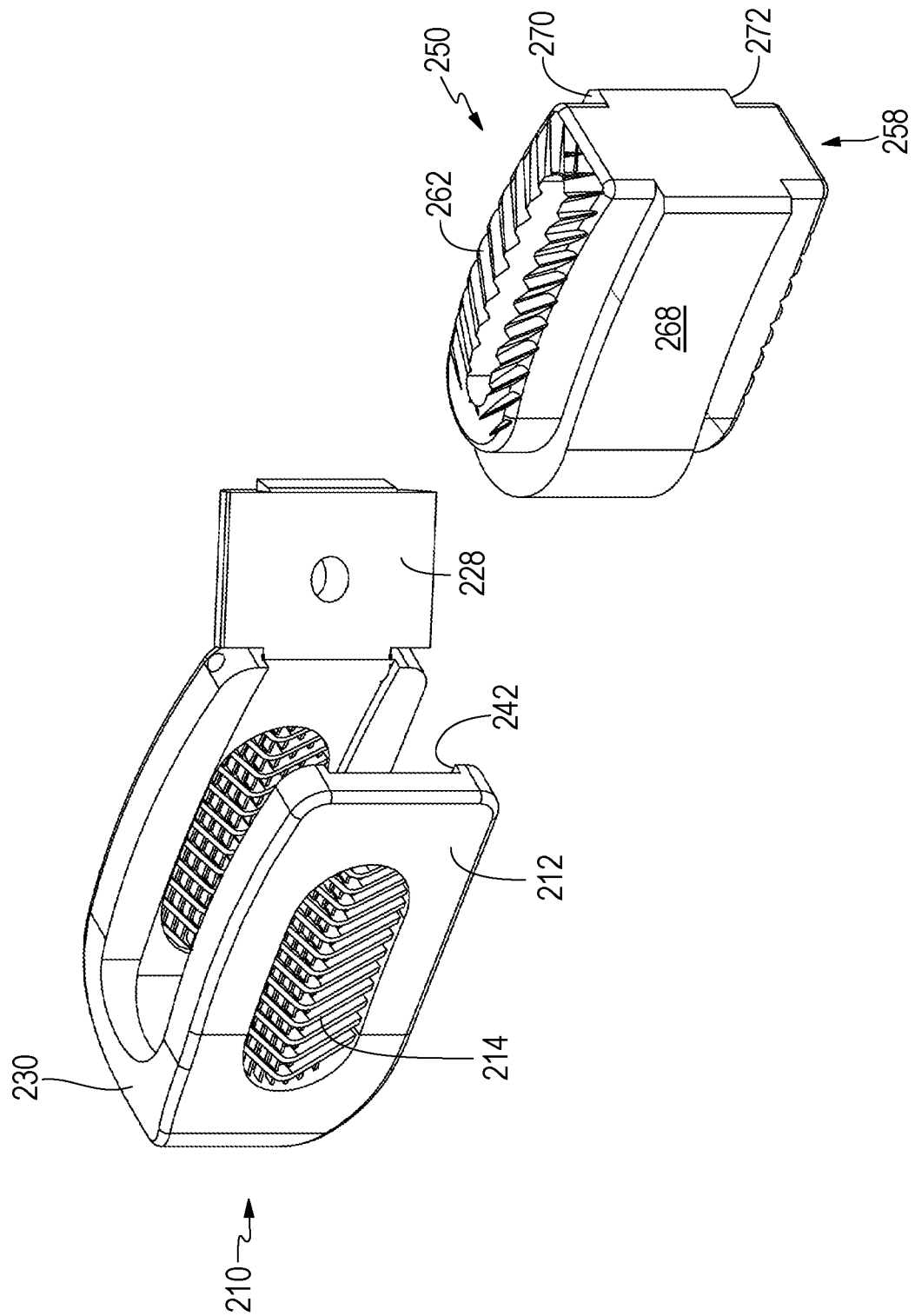
FIG. 30 is an exploded perspective view the posterior end of the TLIF implant of FIG. 18.
Figure 33:
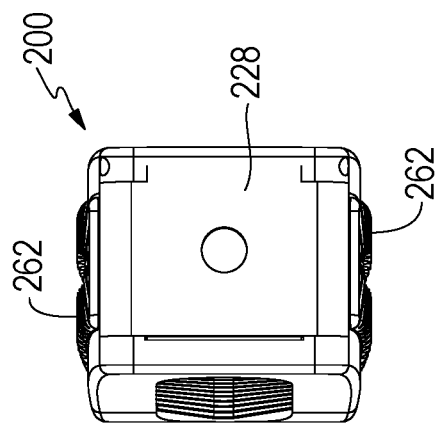
FIG. 33 is a elevational view of a posterior end of TLIF implant of FIG. 18.
Figure 32:
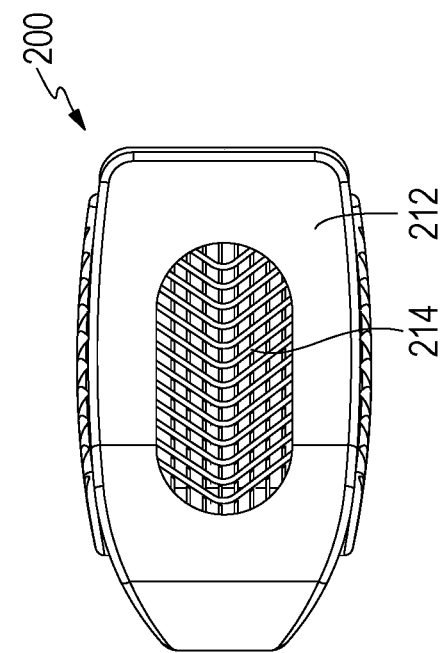
FIG. 32 is a elevational view of a lateral side of the TLIF implant of FIG. 18.
Figure 31:
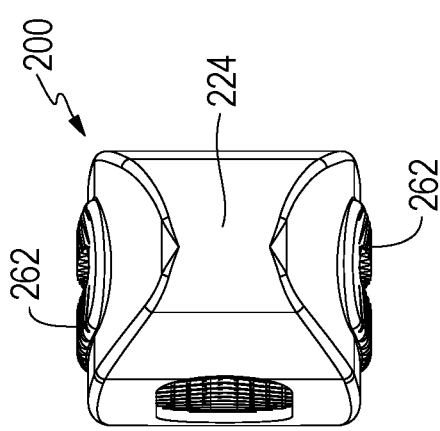
FIG. 31 is a elevational view of THE anterior end of the TLIF implant of FIG. 18.
Figure 34:
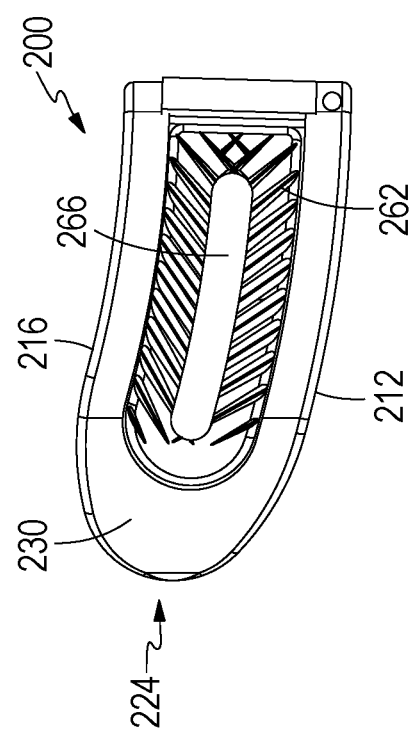
FIG. 34 is a top plan view of the TLIF implant of FIG. 18.

Referring to FIGS. 18 through 34, TLIF implant 200 includes a 3-D printed titanium enclosure 210 having a substantially convex first sidewall 212, a first mesh window 214 extending through the first sidewall, a substantially concave second sidewall 216 opposing the first sidewall, a second mesh window 218 extending through the second sidewall, a substantially convex third sidewall 220 extending to and between the first sidewall and the second sidewall, the third sidewall 220 forming a first end 224 of the enclosure, a second end 226 opposite the first end, a fourth sidewall 228 opposing the third sidewall and hingedly coupled to the second sidewall and detachably coupled to the first sidewall, a substantially U-shaped top wall 230 with a substantially U-shaped top opening 232 there through, and a substantially U-shaped bottom wall 234 with a substantially U-shaped bottom opening 236 there through. The first sidewall, the second sidewall and the third sidewall form a substantially U-shaped sidewall defining a substantially U-shaped slot 238 having an upper seat portion 240 and a lower seat portion 242.

TLIF allograft bone graft 250 includes a substantially convex first face 252, a substantially concave second face 254 opposing the first face, a substantially convex third face 256 extending to and between the first face and the second face, a fourth face 258 opposing the third face having a substantially cross-shaped cross-section, a substantially convex top face 260 including anti-migration ridges 262, a substantially convex bottom face 264 including anti-migration ridges 262, and a hole 266 extending to and between the top face and the bottom face. The first face, the second face and the third face form a substantially U-shaped face including a substantially U-shaped protrusion 268 extending along a length of the U-shaped face and defining a graft upper ledge 270 and a graft lower ledge 272.

In use, fourth sidewall 228 is pivoted open, and TLIF allograft bone graft 250 is inserted into enclosure 210 through the open doorway with the a graft upper ledge 270 engaged with the upper seat portion 1240 and the graft lower ledge 272 engaged with the lower seat portion 242. Fourth sidewall 228 is then closed and fixed shut. Once assembled, TLIF implant 200 may be used to fuse adjacent vertebra according to the method described above, with top and bottom faces 260, 264 protruding out through U-shaped slot 238 so that anti-migration ridges 262 may directly contact adjacent the vertebrae.

ALIF

Figure 36:
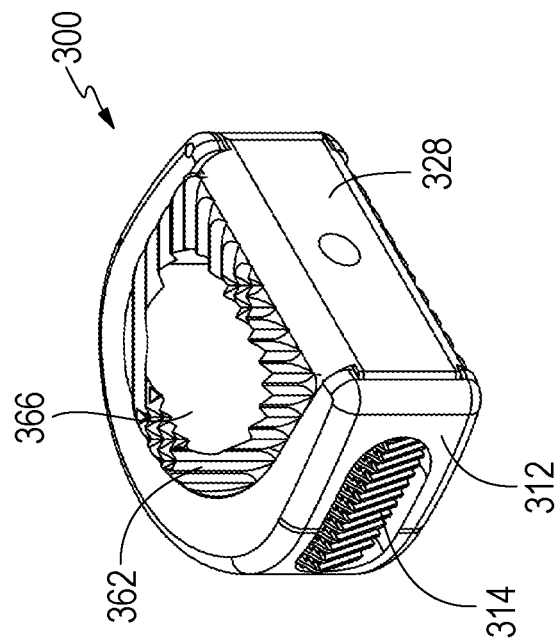
FIG. 36 is a perspective view of a posterior end of the ALIF implant of FIG. 35.
Figure 35:
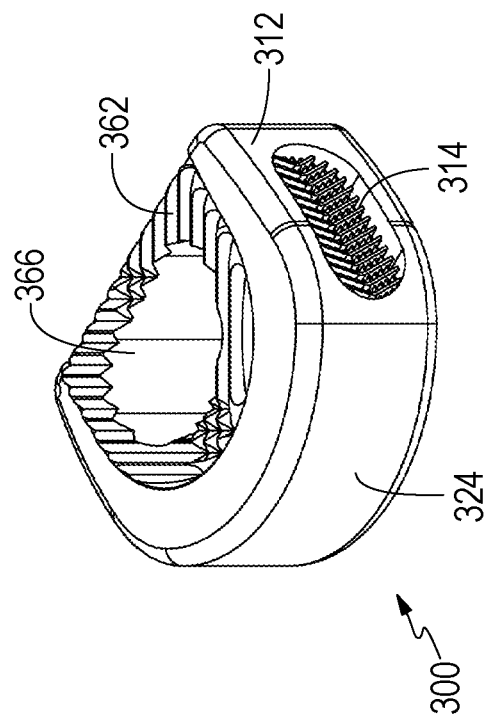
FIG. 35 is a perspective view of an anterior end of a ALIF implant illustrating an allograft bone graft contained with a cage.
Figure 47:
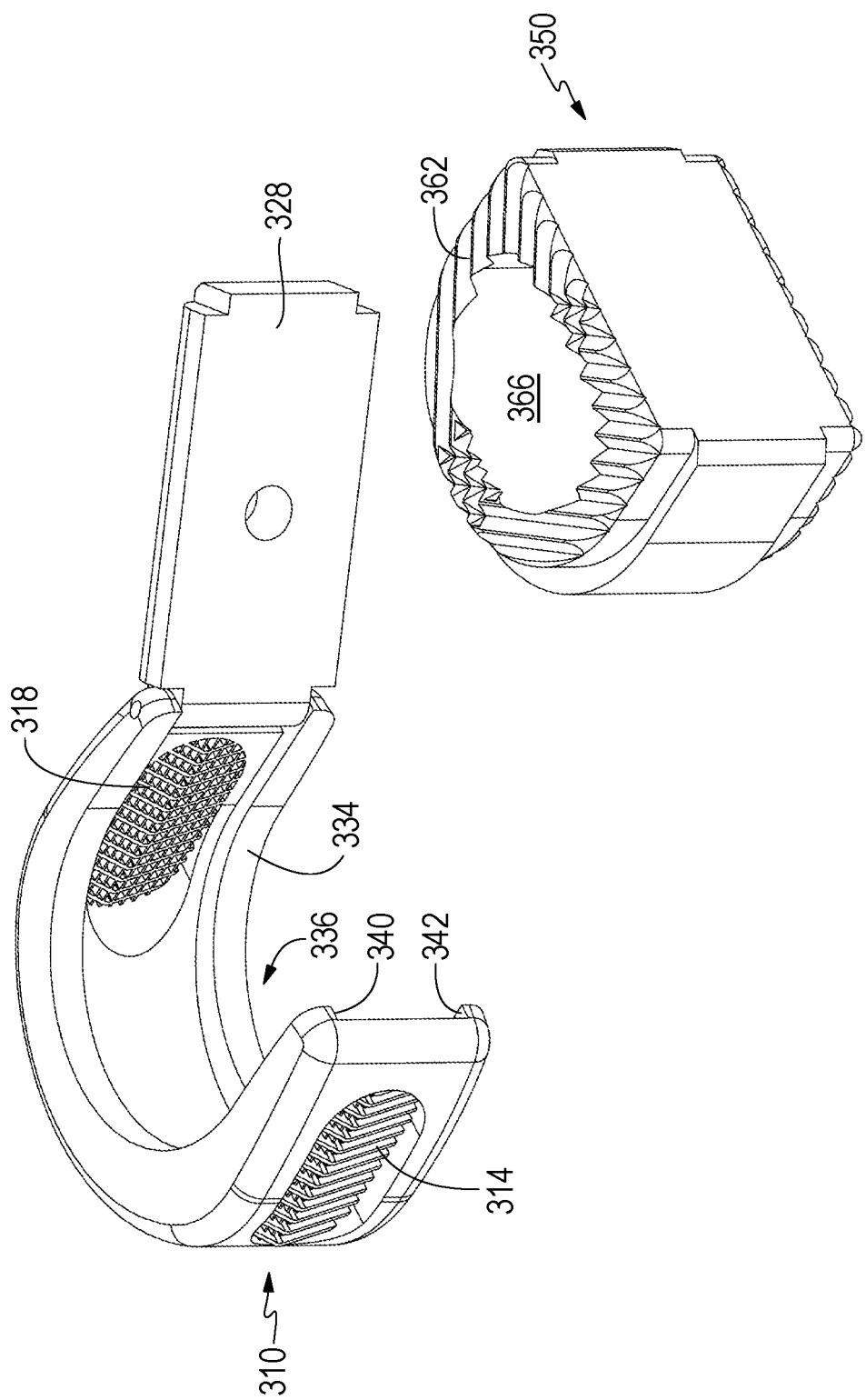
FIG. 47 is an exploded perspective view the posterior end of the ALIF implant of FIG. 35.

Referring to FIGS. 35 through 51, ALIF implant 300 includes a 3-D printed titanium enclosure 310 having a first sidewall 312, a first mesh window 314 extending through the first sidewall, a second sidewall 316 opposing the first sidewall, a second mesh window 318 extending through the second sidewall, a substantially convex third sidewall 320 extending to and between the first sidewall and the second sidewall, the third sidewall 320 forming a first end 324 of the enclosure, a second end 326 opposite the first end, a fourth sidewall 328 opposing the third sidewall and hingedly coupled to the second sidewall and detachably coupled to the first sidewall, a longitudinal axis extending through a center of the third sidewall and a center of the fourth sidewall, a substantially U-shaped top wall 330 with a substantially U-shaped top opening 332 there through, and a substantially U-shaped bottom wall 334 with a substantially U-shaped bottom opening 336 there through. The first sidewall, the second sidewall and the third sidewall form a substantially U-shaped sidewall defining a substantially U-shaped slot 338 having an upper seat portion 340 and a lower seat portion 342. U-shaped slot 338 has a width defined between sidewall 312, 316 that tapers inwardly from first end to 324 to second end 326.

ALIF allograft bone graft 350 includes a first face 352, a second face 354 opposing the first face, a substantially convex third face 356 extending to and between the first face and the second face, wherein the longitudinal axis extends through a center of the third face, a fourth face 358 opposing the third face having a substantially cross-shaped cross-section, wherein the longitudinal axis extends through a center of the fourth face, a top face 360 including anti-migration ridges 362, a bottom face 364 including anti-migration ridges 362, and a hole 366 extending to and between the top face and the bottom face. The first face, the second face and the third face form a substantially U-shaped face including a substantially U-shaped protrusion 368 extending along a length of the U-shaped face and defining a graft upper ledge 370 and a graft lower ledge 372.

In use, fourth sidewall 1328 is pivoted open, and ALIF allograft bone graft 350 is inserted into enclosure 310 through the open doorway with the a graft upper ledge 370 engaged with the upper seat portion 340 and the graft lower ledge 372 engaged with the lower seat portion 342. Fourth sidewall 328 is then closed and fixed shut. Once assembled, ALIF implant 300 may be used to fuse adjacent vertebra according to the method described above, with top and bottom faces 360, 364 protruding out through U-shaped slot 338 so that anti-migration ridges 362 may directly contact adjacent the vertebrae.

DLIF

Referring to FIGS. 52 through 68, DLIF implant 400 includes a 3-D printed titanium enclosure 410 having a first sidewall 412, a pair of first mesh windows 414 extending through the first sidewall, a second sidewall 416 opposing the first sidewall, a pair of second mesh windows 418 extending through the second sidewall, a substantially convex third sidewall 420 extending to and between the first sidewall and the second sidewall, the third sidewall 420 forming a first end 424 of the enclosure, a second end 426 opposite the first end, a fourth sidewall 428 opposing the third sidewall and hingedly coupled to the second sidewall and detachably coupled to the first sidewall, a longitudinal axis extending through a center of the third sidewall and a center of the fourth sidewall, a substantially U-shaped top wall 430 with a substantially U-shaped top opening 432 there through, and a substantially U-shaped bottom wall 434 with a substantially U-shaped bottom opening 436 there through. The first sidewall, the second sidewall and the third sidewall form a substantially U-shaped sidewall defining a substantially U-shaped slot 438 having an upper seat portion 440 and a lower seat portion 442.

DLIF allograft bone graft 450 includes a first face 452, a second face 454 opposing the first face, a substantially convex third face 456 extending to and between the first face and the second face, wherein the longitudinal axis extends through a center of the third face, a fourth face 458 opposing the third face having a substantially cross-shaped cross-section, wherein the longitudinal axis extends through a center of the fourth face, a top face 460 including anti-migration ridges 462, a bottom face 464 including anti-migration ridges 462, and a pair of holes 466 extending to and between the top face and the bottom face. The first face, the second face and the third face form a substantially U-shaped face including a substantially U-shaped protrusion 468 extending along a length of the U-shaped face and defining a graft upper ledge 470 and a graft lower ledge 472.

In use, fourth sidewall 428 is pivoted open, and DLIF allograft bone graft 450 is inserted into enclosure 410 through the open doorway with the a graft upper ledge 470 engaged with the upper seat portion 440 and the graft lower ledge 472 engaged with the lower seat portion 442. Fourth sidewall 428 is then closed and fixed shut. Once assembled, DLIF implant 400 may be used to fuse adjacent vertebra according to the method described above, with top and bottom faces 460, 464 protruding out through U-shaped slot 438 so that anti-migration ridges 462 may directly contact adjacent the vertebrae.

What is claimed:

1. A spinal implant comprising:
   a first sidewall,
   a second sidewall,
   a third sidewall extending to and between the first sidewall and the second sidewall, wherein the first sidewall, the second sidewall and the third sidewall form a substantially U-shaped sidewall defining a slot configured for receiving an allograft and retaining the allograft between the first sidewall and the second sidewall,
   a fourth sidewall configured for enclosing the allograft within the slot,
   an allograft block received and retained within the slot, wherein the allograft block has a lower edge supported on a first lower seat portion formed by the first sidewall and a second lower seat portion formed by the second sidewall.

2. The implant of claim 1, further comprising a first window extending through the first sidewall and a second window extending through the second sidewall.

3. The implant of claim 1, wherein the fourth sidewall is detachably coupled to the first sidewall.

4. The implant of claim 1, further comprising a substantially U-shaped top wall with a substantially U-shaped top opening there through.

5. The implant of claim 1, further comprising a substantially U-shaped bottom wall with a substantially U-shaped bottom opening there through.

6. The implant of claim 1, wherein the first sidewall, the second sidewall, and the third sidewall are fabricated from titanium.

7. A surgical method for vertebral interbody fusion comprising:
   inserting the implant of claim 1 between a first vertebra and a second vertebra,
   wherein the surgical method is a surgical procedure selected from the group consisting of a posterior lumbar interbody fusion procedure, an anterior lumbar interbody fusion procedure, a transforaminal lumbar interbody fusion procedure and a transpsoas interbody fusions procedure.

8. A spinal implant comprising:
a first sidewall,
a second sidewall opposing the first sidewall,
a third sidewall extending to and between the first sidewall and the second sidewall, the third sidewall forming a first end of the implant,
a second end opposite the first end, and
a fourth sidewall,
wherein the first sidewall, the second sidewall and the third sidewall form a substantially U-shaped sidewall defining a slot, the fourth sidewall being configured for selectively enclosing the slot, and
wherein an allograft bone graft is located within the slot between the first sidewall and the second sidewall and between the third sidewall and the fourth sidewall, the allograft bone graft including an edge supported by a seat formed by the first sidewall.

9. The implant of claim 8, wherein the fourth sidewall is detachably coupled to the first sidewall.

10. A spinal implant comprising:
a first sidewall,
a second sidewall,
a substantially convex third sidewall extending to and between the first sidewall and the second sidewall, the third sidewall forming a first end of the spinal implant,
a second end opposite the first end, and
a fourth sidewall configured for selectively covering the second end,
wherein the first sidewall, the second sidewall and the third sidewall form a slot, and
an allograft bone graft received and retained within the slot, the allograft bone graft including an edge supported by a seat formed by the first sidewall.

11. The implant of claim 10, further comprising a top wall with a substantially U-shaped top opening there through and a bottom wall with a substantially U-shaped bottom opening there through.

12. The implant of claim 10, wherein the allograft bone graft is located in the slot between the first sidewall and the second sidewall.

13. The implant of claim 12, wherein the fourth sidewall encloses the allograft bone graft with in the slot.

14. The implant of claim 10, wherein the first sidewall, the second sidewall and the third sidewall form a U-shaped sidewall.

15. A surgical method for vertebral interbody fusion comprising inserting the implant of claim 10 between a first vertebra and a second vertebra.

* * * * *